United States Patent
Tao et al.

(10) Patent No.: US 7,307,258 B2
(45) Date of Patent: Dec. 11, 2007

(54) TERAHERTZ SYSTEM FOR DETECTING THE BURN DEGREE OF SKIN

(75) Inventors: Teh Ho Tao, Hsinchu (TW); Tze An Liu, Jhudong Township (TW); Zu Sho Chow, Jhubei (TW); Sheng Lung Wu, Fongyuan (TW); Ci Ling Pan, Hsinchu (TW)

(73) Assignee: Oki Electric Industry Co., Ltd., Tokyo (JP)

( * ) Notice: Subject to any disclaimer, the term of this patent is extended or adjusted under 35 U.S.C. 154(b) by 0 days.

(21) Appl. No.: 11/258,086

(22) Filed: Oct. 26, 2005

(65) Prior Publication Data

US 2006/0217601 A1    Sep. 28, 2006

(30) Foreign Application Priority Data

Mar. 23, 2005 (TW) .............................. 94108924 A

(51) Int. Cl.
*G01J 5/02* (2006.01)
*H01L 31/00* (2006.01)

(52) U.S. Cl. .................................. 250/341.1; 250/214.1

(58) Field of Classification Search ............. 250/341.1, 250/341.8, 216, 585, 330, 338.1, 358.1, 339.4, 250/214.1; 600/473, 306; 359/326–332; 385/12, 13, 15

See application file for complete search history.

(56) References Cited

U.S. PATENT DOCUMENTS

| | | | | |
|---|---|---|---|---|
| 5,324,935 A * | 6/1994 | Yasutake | ..................... | 250/234 |
| 5,729,017 A * | 3/1998 | Brener et al. | ............. | 250/338.1 |
| 6,847,448 B2 * | 1/2005 | Nagashima et al. | ........ | 356/364 |
| 6,873,165 B2 * | 3/2005 | Lee et al. | .................... | 324/750 |
| 6,909,095 B2 * | 6/2005 | Tran et al. | ................ | 250/341.1 |
| 6,977,379 B2 * | 12/2005 | Zhang et al. | ............. | 250/341.1 |
| 2001/0038074 A1 * | 11/2001 | Zhang et al. | ............. | 250/341.8 |
| 2003/0165003 A1 * | 9/2003 | Ciesla et al. | ................ | 359/326 |
| 2004/0065832 A1 * | 4/2004 | Cluff et al. | .............. | 250/341.1 |
| 2004/0155665 A1 * | 8/2004 | Arnone et al. | .............. | 324/644 |
| 2004/0196660 A1 * | 10/2004 | Usami | ........................ | 362/458 |

* cited by examiner

*Primary Examiner*—Thanh X. Luu
*Assistant Examiner*—Pascal M Bui-Pho
(74) *Attorney, Agent, or Firm*—Volentine & Whitt, P.L.L.C.

(57) ABSTRACT

A system for detecting the burn degree of skin includes a laser source for generating laser light, a light-splitting device for splitting the laser light into a pump beam and a probe beam, a modulation device positioned on the optical path of the pump beam, a sampling device positioned between the light-splitting device and the modulation device, a terahertz pulse emitter for generating terahertz pulses by irradiating of the pump beam, a terahertz pulse detector for detecting the terahertz pulse reflected by a sample, a current detector electrically connected to the terahertz pulse detector, and a phase lock-in amplifier electrically connected to the current detector. The terahertz pulse emitter includes a plurality of photoconductive antennas positioned in an array manner, and the system further includes a first fiber coupler for transmitting the pump beam from the modulation device to the photoconductive antennas of the terahertz pulse emitter.

14 Claims, 4 Drawing Sheets

TERAHERTZ SYSTEM FOR DETECTING THE BURN DEGREE OF SKIN

BACKGROUND OF THE INVENTION (A) Field of the Invention

The present invention relates to a system for detecting the burn degree of skin, and more particularly, to a system for detecting the burn degree of skin using reflective terahertz pulses.

(B) Description of the Related Art

There are four burn degrees of skin; first to fourth, wherein the second burn degree is further subdivided into the deep second degree and the shallow second degree. A burned skin above the deep second degree cannot heal autogenously, and it can only be cured by removing the necrotic skin before performing a grafting skin surgery. To cure burned skin, it is most important to determine the trauma depth of subcutaneous tissue of a patient, which can be used as a judgment basis of whether to remove necrotic skin and grafting skin surgery. Therefore, it appears to be a significant importance to provide equipment in real time manner for a physician to judge the trauma depth of subcutaneous tissue of the patient. When measuring the trauma depth of subcutaneous tissue of a patient by current commercial detection instrument, the patient must be moved onto the support bracket of the instrument and the probe of the instrument must touch the patient. Therefore, the patient will feel uncomfortable. In addition, some pretreatment procedures for these detection instruments are multifarious and the accuracy of the detected data is comparatively low.

There are five types of methods for measuring burned depth, including: (1) biopsy; (2) blood circulation status examination; (3) supersonic inspection; (4) thermal image technology in non-time domain; and (5) thermal image technology in time domain. However, none of the above five methods can offer such advantages as non-contact, non-invasive, indicating burned depth, measuring bloodstream information, at the same time, thus cannot satisfy clinical needs. In addition, U.S. 2003/0149346A1 discloses a detection system using reflective terahertz pulse, which can detect interface of horny layer/horny layer and horny layer/dermis of skin.

SUMMARY OF THE INVENTION

A system for detecting the burn degree of skin comprises a laser source for generating a laser light, a light-splitting device for splitting the laser light into a pump beam and a probe beam, a modulation device positioned on the optical path of the pump beam, a sampling device positioned between the light-splitting device and the modulation device, a terahertz pulse emitter for generating terahertz pulses by the irradiating of the pump beam, a terahertz pulse detector for detecting the terahertz pulse reflected by a sample, a current detector electrically connected to the terahertz pulse detector, and a phase lock-in amplifier electrically connected to the current detector. The terahertz pulse emitter includes a plurality of photoconductive antennas positioned in an array manner, and the system further comprises a first fiber coupler for transmitting the pump beam from the modulation device to the photoconductive antennas of the terahertz pulse emitter.

Compared to the prior art, the present system for detecting the burn degree of skin detects the depth of an interface between a burned region and a normal region in a non-contact and non-invasive manner so as to prevent the patient from feeling uncomfortable during detection. In addition, the present system for detecting the burn degree of skin can acquire the blood flow information in blood vessels in subcutaneous tissue, which can be used as judgment basis for physicians.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
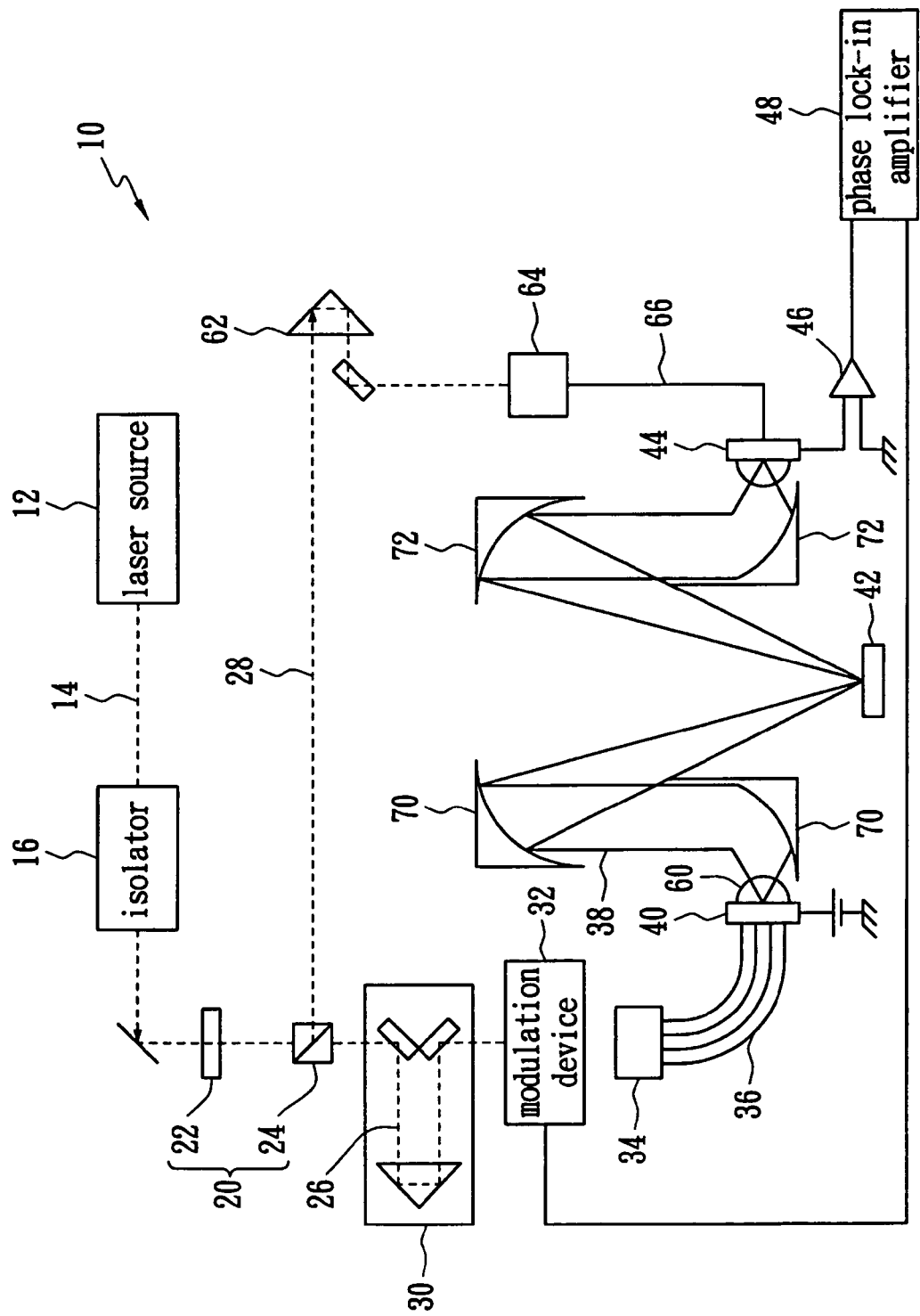
FIG. 1 illustrates a system for detecting the burn degree of skin according to one embodiment of the present invention.

FIG. 1 illustrates a system 10 for detecting the burn degree of skin according to one embodiment of the present invention. The system 10 comprises a laser source 12 for generating a laser light 14, a light-splitting device 20 for splitting the laser light 14 into a pump beam 26 and a probe beam 28, a modulation device 32 positioned on the optical path of the pump beam 26, a sampling device 30 positioned between the light-splitting device 20 and the modulation device 32, a terahertz pulse emitter 40 for generating terahertz pulses 38 by the irradiating of the pump beam 26, a terahertz pulse detector 44 for detecting the terahertz pulse 38 reflected by a sample 42, a current detector 46 electrically connected to the terahertz pulse detector 44, and a phase lock-in amplifier 48 electrically connected to the current detector 46. The photoconductive antenna includes a plurality of photoconductive antennas positioned in an array manner, and the system further comprises a first fiber coupler for transmitting the pump beam from the modulation device to the photoconductive antennas of the terahertz pulse emitter.

The probe beam 28 is transmitted to the terahertz pulse detector 44 via a delay line 62, a fiber coupler 64 and an optical fiber. The system 10 may further comprise an isolator 16 positioned between the laser source 12 and the light-splitting device 20, and the isolator 16 is used to isolate reflective light so as to avoid noise originated from multiple reflections. The terahertz pulses 38 are collected and focused on the sample 42 by two off-axis parabolic mirrors 70, and the reflected terahertz pulses 38 from the sample 42 are collected and focused on the terahertz pulse detector 44 by two off-axis parabolic mirrors 72.

Preferably, the modulation device 32 can be a chopper, the terahertz pulse emitter 40 includes a plurality of photoconductive antennas 50 positioned in an array manner, and the pump beam 26 modulated by the modulation device 32 is transmitted to photoconductive antenna 50 of the terahertz pulse emitter 40 via a fiber coupler 34 and a plurality of fibers 36. The light-splitting device 20 comprises a half-wavelength plate 22 positioned on the optical path of the laser light 14 and a splitter 24 configured to transmit a horizontal component of the laser light 14 to form the pump beam 26 and to reflect the vertical component of the laser light 14 to form the probe beam 28, wherein the power ratio of the pump beam 26 to the probe beam 28 is between 60:40 and 80:20, preferably 70:30.

Figure 2:
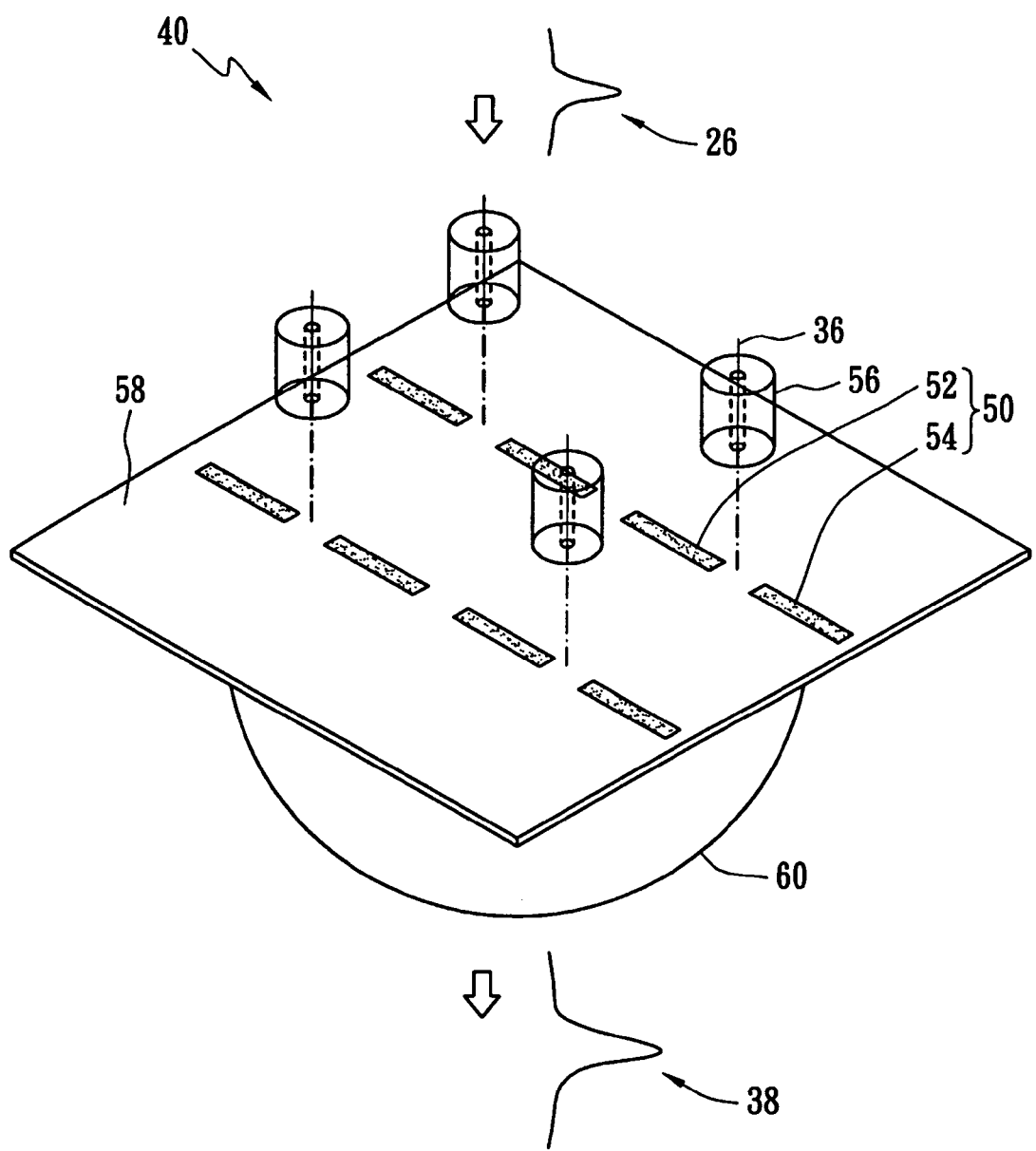
FIG. 2 illustrates the terahertz pulse emitter according to one embodiment of the present invention.

FIG. 2 illustrates the terahertz pulse emitter 40 according to one embodiment of the present invention. The terahertz pulse emitter 40 comprises a substrate 58, a plurality of photoconductive antenna 50 positioned on the substrate 58 in an array manner, and a silicon lens 60 positioned on the back surface of the substrate 58. The photoconductive antenna 50 includes a first conductive segment 52 and a second conductive segment 54 positioned on the front surface of the substrate 58, and the optical fiber 36 is fixed between the first conductive segment 52 and the second conductive segment 54 by a sheath 56. In short, the pump beam 26 is transmitted to a region between the biased first conductive segment 52 and the biased second conductive segment 54 to generate the terahertz pulses 38.

Since water molecules in a human body can absorb terahertz pulses, the power of terahertz pulses must be enhanced to measure physiology information deeply under skin (for example, bloodstream information of blood vessels under skin). However, it is impracticable to enhance power of the terahertz pulse 38 by increasing the power of the pump beam 26 due to the saturation effect of the photoconductive antenna 50. The present invention solves the saturation effect of the photoconductive antenna 50 by using the terahertz pulse emitters 40 consisting of several photoconductive antennas 50, so that the present invention can be used to measure physiology information deeply under skin.

Figure 3:
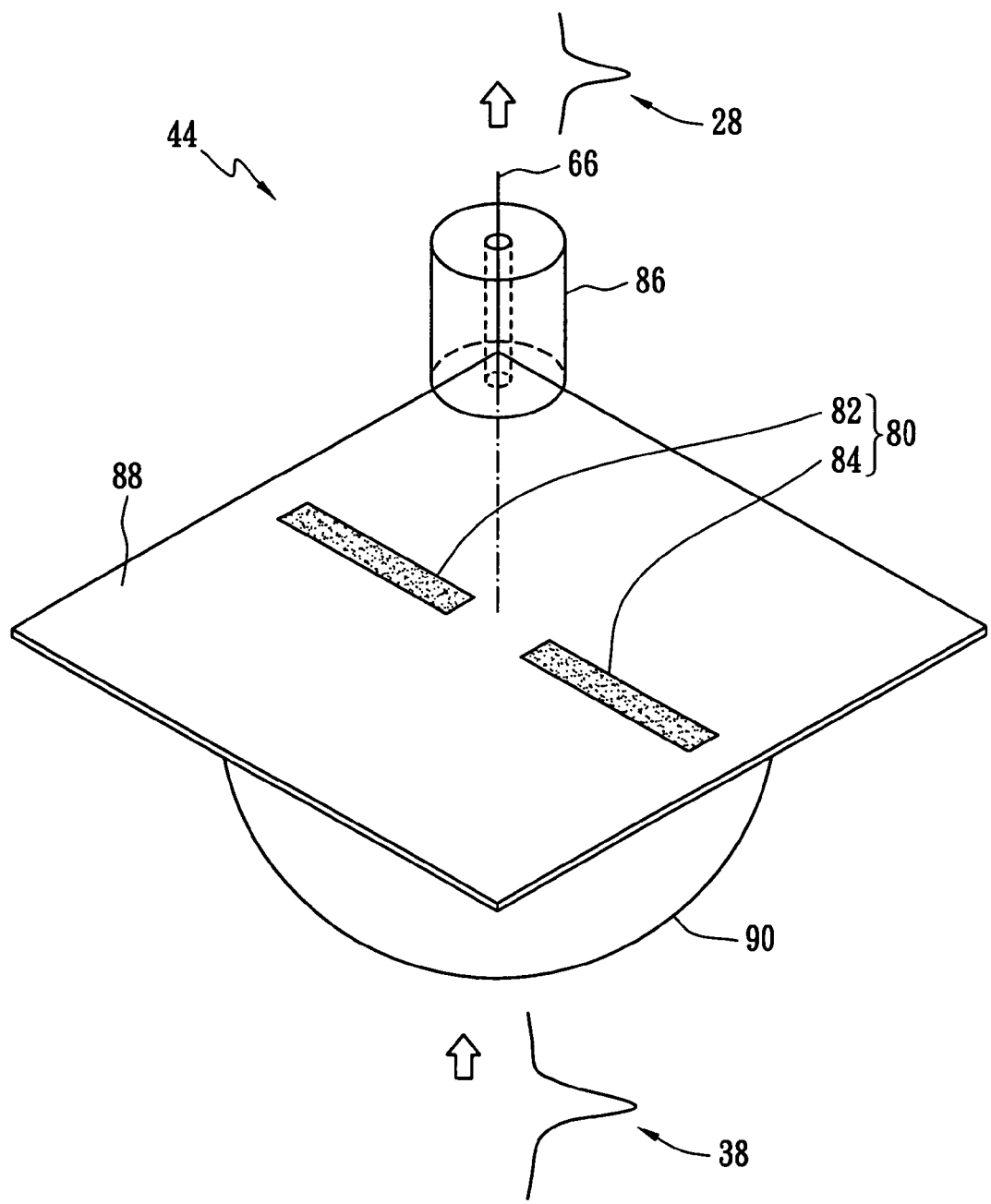
FIG. 3 illustrates the terahertz pulse detector according to one embodiment of the present invention.

FIG. 3 illustrates the terahertz pulse detector 44 according to one embodiment of the present invention. The terahertz pulse detector 44 comprises a substrate 88, a photoconductive antenna 80 positioned on the substrate 88 and a silicon lens 90 positioned on the back surface of the substrate 88. The photoconductive antenna 80 includes a first conductive segment 82 and a second conductive segment 84 positioned on the front surface of the substrate 88, and the optical fiber 66 is secured between the first conductive segment 82 and the second conductive segment 84 of the photoconductive antennas 80 by a sheath 86. The probe beam 28 irradiates at a region between the first conductive segment 82 and the second conductive segment 84 of the photoconductive antennas 80 simultaneously along with terahertz pulse 38 reflected by the sample 40 so as to generates photocurrent proportional to the intensity of the electric field of the terahertz pulse 38 between the first conductive segment 82 and the second conductive segment 84. The current detector 46 senses the intensity of the photocurrent via the first conductive segment 82 and second conductive segment 84, and the phase lock-in amplifier 48 demodulates the measurement signal from the current detector 46 based on the modulation signal of the modulation device 32.

Figure 4:
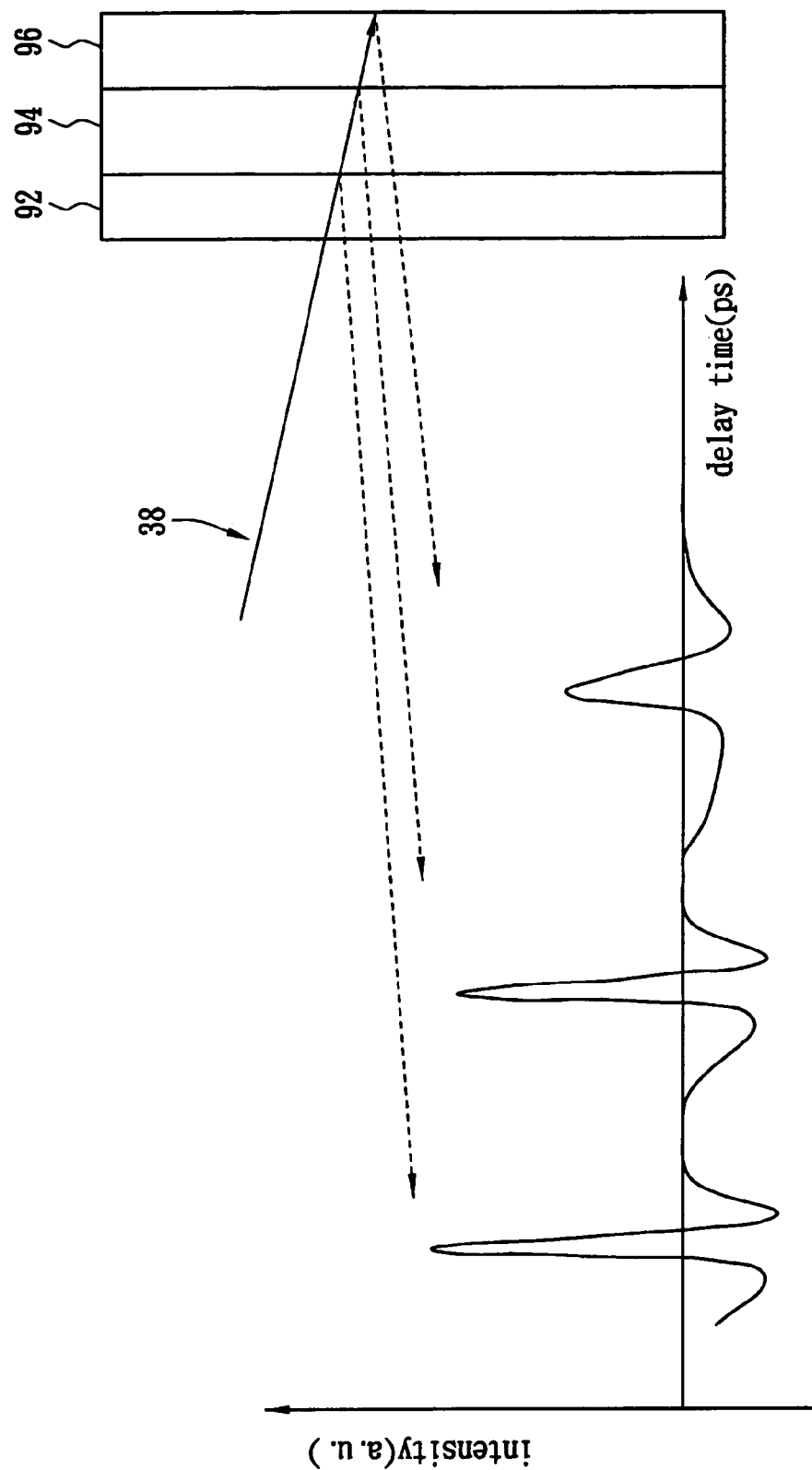
FIG. 4 illustrates the application of the system for detecting the burn degree of skin according to one embodiment of the present invention.

FIG. 4 illustrates the application of the system 10 to the measurement of the interface depth between a burned skin 92 and a normal skin 94 and bloodstream information of a subcutaneous blood vessel 96. Since 0.8 THz and 1.4 THz terahertz pulse is resonant modes of the hemoglobin, hemoglobin in the blood vessel 96 can absorb terahertz pulses in the band between 0.2 THz to 1.6 THz strongly. In addition, the interface between the burned skin 92 and the normal skin 94 can also reflect the terahertz pulse 38. Consequently, the system 10 can measure the interface depth between the burned skin 92 according to the delay time of the reflected terahertz pulse 38, and the bloodstream information of a subcutaneous blood vessel 96 can be determined from the absorption intensity of the of the hemoglobin in the blood vessel 94 to the terahertz pulse 38.

Compared to the prior art, the present system for detecting the burn degree of skin detects the depth of an interface between a burned region and a normal region in a non-contact and non-invasive manner so as to prevent the patient from feeling uncomfortable during detection. In addition, the present system for detecting the burn degree of skin can acquire the blood flow information in blood vessels in subcutaneous tissue, which can be used as judgment basis for doctors.

The above-described embodiments of the present invention are intended to be illustrative only. Numerous alternative embodiments may be devised by those skilled in the art without departing from the scope of the following claims.

What is claimed is:

1. A system for detecting the burn degree of skin, comprising:
   a laser source for generating laser light;
   a light-splitting device for splitting the laser light into a pump beam and a probe beam;
   a modulation device positioned on an optical path of the pump beam;
   a terahertz pulse emitter including a plurality of photoconductive antennas positioned in an array on a first surface of a substrate, the substrate having a lens disposed on a second surface of the substrate opposite the first surface, wherein the photoconductive antennas are irradiated by the pump beam so as to generate terahertz pulses emitted to burned skin;
   a first fiber coupler configured to transmit the pump beam from the modulation device to the photoconductive antennas of the terahertz pulse emitter via a plurality of fibers;
   at least one parabolic mirror configured to collect and focus the terahertz pulses on the burned skin;
   a terahertz pulse detector for detecting the terahertz pulses reflected by the burned skin, wherein the probe beam is coupled with the terahertz pulse detector;
   a current detector electrically connected to the terahertz pulse detector;
   a phase lock-in amplifier electrically connected to the current detector: and
   a second fiber coupler positioned between the light-splitting device and the terahertz pulse detector.

2. The system for detecting the burn degree of skin of claim 1, wherein the light-splitting device comprises:
   a half-wavelength plate positioned on the optical path of the laser light; and
   a splitter configured to transmit a horizontal component of the laser light to form the pump beam and to reflect a vertical component of the laser light to form the probe beam.

3. The system for detecting the burn degree of skin of claim 1, wherein a power ratio of the pump beam to the probe beam is between 60:40 and 80:20.

4. The system for detecting the burn degree of skin of claim 1, further comprising a sampling device positioned between the light-splitting device and the modulation device.

5. The system for detecting the burn degree of skin of claim 1, further comprising an isolator positioned between the laser source and the light-splitting device.

6. The system for detecting the burn degree of skin of claim 1, wherein the modulation device is a chopper.

7. The system for detecting the burn degree of skin of claim 6, wherein the chopper is electrically connected to the phase lock-in amplifier.

8. An optical detecting system comprising:
   a laser source that generates laser light;
   a light-splitting device that splits the laser light into a pump beam and a probe beam;
   a modulation device positioned on an optical path of the pump beam;
   a terahertz pulse emitter array including a plurality of photoconductive antennas on a first surface of a substrate, the substrate having a lens disposed on a second surface opposite the first surface, wherein the photoconductive antennas are each irradiated by the pump beam so as to generate respective terahertz pulses that are emitted to burned skin;
   a first fiber coupler having a plurality of fibers that respectively transmit the pump beam to the photoconductive antennas of the terahertz pulse emitter array;
   at least one parabolic mirror configured to collect and focus the terahertz pulses on the burned skin;
   a terahertz pulse detector that detects the terahertz pulses reflected by the sample to provide a detection signal, wherein the probe beam is coupled with the terahertz pulse detector;
   a current detector electrically connected to the terahertz pulse detector, that detects a current of the detection signal to provide a measurement signal;
   a phase lock-in amplifier that demodulates the measurement signal; and
   a second fiber coupler positioned between the light-splitting device and the terahertz pulse detector.

9. The optical detecting system of claim 8, wherein the light-splitting device comprises:
   a half-wavelength plate positioned on the optical path of the laser light; and
   a splitter configured to transmit a horizontal component of the laser light passed by the half-wavelength plate to form the pump beam and to reflect a vertical component of the laser light passed by the half-wavelength plate to form the probe beam.

10. The optical detecting system of claim 8, wherein a power ratio of the pump beam to the probe beam is between 60:40 and 80:20.

11. The optical detecting system of claim 8, further comprising a sampling device positioned between the light-splitting device and the modulation device.

12. The optical detecting system of claim 8, further comprising an isolator positioned between the laser source and the light-splitting device.

13. The optical detecting system of claim 8, wherein the modulation device is a chopper.

14. The optical detecting system of claim 13, wherein the chopper is electrically connected to the phase lock-in amplifier.

* * * * *

UNITED STATES PATENT AND TRADEMARK OFFICE
CERTIFICATE OF CORRECTION

PATENT NO.          : 7,307,258 B2                                        Page 1 of 1
APPLICATION NO.     : 11/258086
DATED               : December 11, 2007
INVENTOR(S)         : Teh Ho Tao et al.

It is certified that error appears in the above-identified patent and that said Letters Patent is hereby corrected as shown below:

Title Page;

The correct Assignee (73) should be listed as:

Industrial Technology Research Institute, Hsinchu County 310 Taiwan

Signed and Sealed this

Twenty-second Day of September, 2009

David J. Kappos
*Director of the United States Patent and Trademark Office*